United States Patent [19]

Wood

[11] Patent Number: 4,616,087

[45] Date of Patent: Oct. 7, 1986

[54] 2,5-BIS ALKYL SULFONYL AND 2,5-BIS ALKYL THIO SUBSTITUTED-PYRIDINES

[75] Inventor: Steven G. Wood, Orem, Utah

[73] Assignee: The Dow Chemical Company, Midland, Mich.

[21] Appl. No.: 380,642

[22] Filed: May 21, 1982

[51] Int. Cl.$^4$ .................. C07D 211/72; C07D 211/84
[52] U.S. Cl. ..................................... 546/294; 546/296
[58] Field of Search ........................ 546/296, 290, 294

[56] References Cited

U.S. PATENT DOCUMENTS

| | | | |
|---|---|---|---|
| 3,146,237 | 8/1964 | Robinson | 546/296 |
| 3,317,549 | 5/1967 | Johnston | 546/345 |
| 3,535,328 | 10/1970 | Zielinski | 546/296 |
| 3,549,647 | 12/1970 | Johnston | 546/296 |
| 3,639,413 | 2/1972 | Domenico | 546/296 |
| 3,687,959 | 8/1972 | Zielinski | 546/296 |
| 3,719,682 | 3/1973 | Domenico | 546/296 |
| 3,732,234 | 5/1973 | Domenico | 546/296 |
| 3,954,782 | 5/1976 | Fleckenstein et al. | 546/296 |
| 3,956,294 | 5/1976 | Fleckenstein et al. | 546/296 |
| 4,371,537 | 2/1983 | Markley et al. | 546/296 |

OTHER PUBLICATIONS

Finch et al., J. of Med. Chem., 1978, vol. 21, No. 12, p. 1269 ff.
Ponticello et al., J. Org. Chem., vol. 44, No. 17, 1979, p. 3080, ff.
Blank et al., J. of Med. Chem., vol. 20, 1977, No. 12, p. 1572 ff.
Finch et al., J. Org. Chem., vol. 40, No. 5, 1975, p. 569 ff.
Newkome, G. et al., J. Organometallic Chemistry, 186, pp. 147-153, (1980).
Chem. Abs., 95, 80748z (1981) Ruth, Ann. Chem., 487, pp. 105-119 (1931).
Wuest, H. M. et al., J. Am. Chem. Soc., 73, pp. 1210-1216 (1951).
Chen et al., J. Chem. Soc., Chem. Commun., pp. 1139-1140 (1980).
Krowicki, K., Polish J. Chem., 53, pp. 503-506, 701-707 and 889-892 (1979).
Bottino et al., J. Heterocyclic Chem., 18, pp. 199-200 (1981).
Krowicki, K. et al., Rolzniki Chemii, 51, pp. 2435-2438 (1977).
Krowicki, K., Polish J. Chem., 52, pp. 2039-2044 (1978).
Martani et al., Boll. Chim. Farm., 114, pp. 590-597 (1975).
Mitsubishi, Chem. Ind., KK-J5-6061-354.
Krowicki, K., Polish J. Chem., 53(4), 1979, Mercaptopyridine Synthesis.
Chem. Abs., vol. 68, 1968, 104,913v.
Chem. Abs., vol. 71, 1969, 112,761w.

*Primary Examiner*—Henry R. Jiles
*Assistant Examiner*—Robert C. Whittenbaugh

[57] ABSTRACT

A process for preparing substituted-pyridines having a sulfonyl type substituted at the 3 or 5 position of the pyridine ring and a phenoxy type substituent at the 2 position is described.

20 Claims, No Drawings

2,5-BIS ALKYL SULFONYL AND 2,5-BIS ALKYL THIO SUBSTITUTED-PYRIDINES

SUMMARY OF THE INVENTION

The present invention is directed to a novel process for preparing substituted-pyridines having a sulfonyl type substituent at the 3 or 5 position of the pyridine ring and a phenoxy type substituent at the 2 position. In the process, a 3,6- or 5,6-dihalo-2-pyridinecarboxylic acid (or their methyl ester) is reacted with a mercaptan to form a 3,6- or 5,6-bis-(R-thio)-2-pyridinecarboxylic acid of the formula:

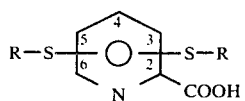 (I)

wherein the R—R— moieties are attached to the pyridine ring either at the 3 and 6 positions or 5 and 6 positions; and R represents a straight or branched chain alkyl group of from 1 to 7 carbon atoms, inclusive, such as methyl, ethyl, propyl, isopropyl, t-butyl, n-hexyl and n-heptyl, a cycloalkyl group of 5 or 6 carbon atoms, such as cyclopentyl and cyclohexyl, or a Ar—$(CH_2)_q$— group wherein q represents the integer 0, 1, 2 or 3 and Ar represents an aryl group of from 6 to 10 carbon atoms, inclusive, which aryl group is optionally substituted with 1 to 3 substituents each independently selected from bromo, chloro, fluoro, methyl or methoxy.

The 3,6- or 5,6-bis(R-thio)-2-pyridinecarboxylic acids are utilized to make other intermediates represented by the formula:

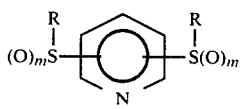 (II)

wherein the

moieties are attached to the pyridine ring either at the 2 and 5 positions or 2 and 3 positions; m represents the integer 0 or 2; and R is as defined for formula I.

Those compounds of formula II wherein m is 0, i.e., the 2,3- or 2,5-bis(R-thio)pyridines are prepared by decarboxylating the 3,6- or 5,6-bis(R-thio)-2-pyridinecarboxylic acids.

Those compounds of formula II wherein m is 2, i.e., the 2,3- or 2,5-bis(R-sulfonyl)pyridines are prepared by oxidizing the 2,3- or 2,5-bis(R-thio)pyridines.

The 2,3- or 2,5-bis(R-sulfonyl)pyridines are extremely useful in that the R-sulfonyl substituent at the 2 position of the pyridine ring is readily amenable to substitution, thus a wide variety of useful compounds can be prepared having a R-sulfonyl group at the 3 or 5 position of the pyridine ring and a phenoxy type substituent at the 2 position. For example, the 2,3- or 2,5-bis(R-sulfonyl)pyridines can be reacted with suitable phenols to produce compounds having antiviral activity.

As used herein, representative Ar—$(CH_2)_q$— groups and substituted—Ar—(—$CH_2)_q$— groups are, for example, phenyl, 4-chlorophenyl, 4-bromophenyl, 4-fluorophenyl, 4-methylphenyl, 4-methoxyphenyl, 3-chlorophenyl, 2-chlorophenyl, 2,3-dichlorophenyl, 2,4-dichlorophenyl, 3,4-dichlorophenyl, 3-bromo-4-chlorophenyl, 4-methyl-2-chlorophenyl, 2-methyl-4-chlorophenyl, 2,4-dimethylphenyl, 2,4,6-trichlorophenyl, 3,4,5-trichlorophenyl, 4-methyl-2,6-dichlorophenyl, 2-bromo-4-methyl-6-chlorophenyl, naphthyl, 6-chloronaphthyl, 6-methylnaphthyl, 6,7-dichloronaphthyl, 6,7-dimethylnaphthyl, benzyl, 4-chlorobenzyl, 4-bromobenzyl, 4-fluorobenzyl, 4-methylbenzyl, 4-methoxybenzyl, 3-chlorobenzyl, 2-chlorobenzyl, 2,4-dichlorobenzyl, 3,4-dichlorobenzyl, 4-methyl-2-chlorobenzyl, 2-methyl-4-chlorobenzyl, 2,4-dimethylbenzyl, 2,4,6-trichlorobenzyl, 3,4,5-trichlorobenzyl, 4-methyl-2,6-dichlorobenzyl, and similar unsubstituted and substituted phenylethyl, phenylpropyl, phenylisopropyl, naphthylmethyl, naphthylethyl, naphthylpropyl and naphthylisopropyl moieties.

DETAILED DESCRIPTION OF THE INVENTION

The process of the present invention is more fully described as follows:

A 3,6-dihalo-2-pyridinecarboxylic acid or a 5,6-dihalo-2-pyridinecarboxylic acid (or their methyl ester) represented by the formula:

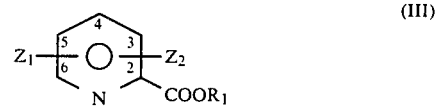 (III)

wherein $Z_1$ and $Z_2$ are attached to the pyridine ring at either the 3 and 6 positions or 5 and 6 positions; $Z_1$ and $Z_2$ each independently represent chloro, bromo, fluoro or iodo; and $R_1$ is hydrogen or methyl; is reacted with the appropriate mercaptan of the formula R—SH, wherein R is defined as for formula I. In the reaction of the dihalo-2-pyridinecarboxylic acid and the mercaptan a dichloro-2-pyridinecarboxylic acid or its methyl ester is preferred.

U.S. Pat. No. 3,317,549 describes 3,6-dichloro-2-pyridinecarboxylic acid and related esters. The compound 5,6-dichloro-2-pyridinecarboxylic acid is readily prepared from 2,3-dichloro-6-(trichloromethyl)pyridine (see U.S. Pat. No. 4,256,894) by hydrolysis employing the procedure described in U.S. Pat. No. 3,317,549.

When $R_1$ is methyl, the above reaction is conveniently accomplished by contacting and mixing the dihalo-2-pyridinecarboxylic acid methyl ester with the mercaptan in a suitable organic solvent, such as dimethylformamide (DME) or dimethyl sulfoxide, in the presence of a base such as potassium t-butoxide (t-BuOK), sodium hydroxide or potassium hydroxide, at from about 100° C. to reflux temperature for a time sufficient to obtain the desired 3,6-bis(R-thio)-2-pyridinecarboxylic acid salt or 5,6-bis(R-thio)-2-pyridinecarboxylic acid salt. Usually a reaction time of about 1 to 10 hours is sufficient for the above reaction.

In the preferable method, when $R_1$ is hydrogen, the reaction is readily accomplished by contacting and mixing the dihalo-2-pyridinecarboxylic acid and the mercaptan in a suitable organic solvent, preferably dimethyl sulfoxide (DMSO), in the presence of a base, such as an alkali metal hydroxide at from about 100° C. to about 150° C. for a time sufficient (usually from about 1 to about 10 hours) to obtain the 3,6-bis(R-thio)-2-pyridinecarboxylic acid salt or 5,6-bis(R-thio)-2-pyridinecarboxylic acid salt.

The above described conditions are sufficient to obtain the desired bis(R-thio)-2-pyridinecarboxylic acid salt; however, longer or shorter reaction times and different reaction temperatures may be utilized in some situations.

The carboxylic acid salt formed by either of the procedures described above is converted to the corresponding acid utilizing conventional procedures, for example, by treating the carboxylic acid salt with an organic acid or mineral acid to give the 3,6-bis(R-thio)-2-pyridinecarboxylic acids or the 5,6-bis(R-thio)-2-pyridinecarboxylic acids, that is, the bis(R-thio)-2-pyridinecarboxylic acids represented by formula I.

Although the use of different proportions of reactants is not detrimental to the above reactions, when $R_1$ is methyl, it is preferable to use about a 3:1 molar ratio of the mercaptan to the dihalo-2-pyridinecarboxylic acid methyl ester; and when $R_1$ is hydrogen, about a 2:1 molar ratio of the mercaptan to the dihalo-2-pyridinecarboxylic acid is preferred.

The bis(R-thio)-2-pyridinecarboxylic acid described above is then decarboxylated to form a bis(R-thio)pyridine of the formula:

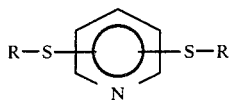

(IV)

wherein the R—S— moieties are attached to the pyridine ring either at the 2 and 5 positions or 2 and 3 positions; and R is as defined for formula I.

Conventional procedures can be used for the above described decarboxylation. For example, the bis(R-thio)-2-pyridinecarboxylic acid can be heated directly (often accompanied by reduced pressure as can be achieved in a Kügelrohr distillation apparatus) or heated in a suitable solvent employed as a heat transfer agent. Suitable solvents for use as heat transfer agents are, for example, decahydronaphthalene, xylene, 1,2-dichlorobenzene, diphenyl ether and other inert high boiling solvents. The choice of the procedure used for decarboxylation depends upon the properties of the compound to be decarboxylated. For example, the Kügelrohr distillation procedure requires that the bis(R-thio)-2-pyridinecarboxylic acid be in a liquid state when decarboxylation is occurring, thus the decarboxylation temperature should fall between the melting point and the boiling point of the compound.

The bis(R-thio)pyridine is then oxidized to a bis(R-sulfonyl)pyridine of the formula:

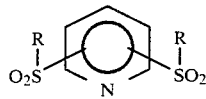

(V)

wherein the

moieties are attached to the pyridine ring either at the 2 and 5 positions or 2 and 3 positions; and R is as defined for formula I.

The above described oxidation is readily accomplished employing well known procedures. Considerations such as the solubility and reactivity of the bis(R-thio)pyridine and the ease of product recovery can dictate the choice of the most appropriate oxidizing agent and conditions to be employed for the oxidation. Oxidizing agents such as hydrogen peroxide/glacial acetic acid, hydrogen peroxide/trifluoroacetic acid, gaseous chlorine in aqueous media, m-chloroperbenzoic acid and other organic peracids and the like can be used for the oxidation.

The bis(R-sulfonyl)pyridine represented by formula V can be reacted with suitable phenols to prepare useful end products. Various 2,3- or 2,5-bis(R-sulfonyl)pyridines described herein have been reacted with substituted-phenols to obtain compounds having antiviral activity. Compounds prepared by the reaction of a 2,3- or 2,5-bis(R-sulfonyl)pyridine and a substituted-phenol are set forth herein and were prepared using the following procedure.

The reaction of the bis-(R-sulfonyl)pyridine and the substituted-phenol is conveniently accomplished by contacting and mixing the reactants in a suitable inert organic solvent in the presence of a base at a temperature of from about 40° C. to about 100° C. for a time sufficient to obtain the desired product. Usually a reaction time of about ½ to about 24 hours is sufficient to obtain a satisfactory yield of the product.

Suitable inert organic solvents are, for example, tetrahydrofuran (THF), 1,4-dioxane, 1,2-dimethoxyethane, isopropanol and other similar sec. and tert.-alcohols. In some cases a quantity of dimethyl sulfoxide may be included to facilitate the reaction. The base should be of sufficient basicity and in sufficient concentration to convert the phenol to its salt for reaction with the appropriate bis(R-sulfonyl)pyridine, such as potassium t.-butoxide, potassium carbonate and alkali metal hydroxides. The reactants can be combined in various proportions, however, the reactants are consumed in equimolar proportions and the use of approximately equimolar proportions is preferred. In some instances (for the less reactive compounds), it may be advantageous to combine and preheat the substituted-phenol and the base in the inert organic solvent prior to the addition of the bis(R-sulfonyl)pyridine.

The following examples are included to provide a better understanding of the invention but are not to be construed as a limitation thereon.

EXAMPLE 1

3,6-bis(methylthio)-2-pyridinecarboxylic acid

Methanethiol (CH$_3$SH), (30.26 g) was dissolved in 200 milliliters (ml) of DMF that had been chilled in Dry Ice to below 0° C. To this solution was added 70.6 grams (g) of potassium t-butoxide (t-BuOK) while the temperature was maintained below 10° C. The resulting white slurry was added to a mixture of 39.35 g of methyl 3,6-dichloro-2-pyridinecarboxylate in 100 ml of DMF. The reaction was heated to 80° C. during the addition and after the addition was complete the temperature was raised to 100° C. and maintained there for 2 hours (hrs). Upon cooling the resulting paste was diluted with ether and filtered. The salts which were obtained were taken up in water, washed with CH$_2$Cl$_2$, and the aqueous phase made acidic with concentrated HCl to pH 3. The resulting solid was filtered and dried on a porous plate which gave 37 g (82% yield) of the crude product as a bright yellow solid. A portion of the crude product was recrystallized from ethanol, which gave purified 3,6-bis(methylthio)-2-pyridinecarboxylic acid as bright yellow plates, which was found to have a melting point (m.p.) of 142°–144° C.

EXAMPLE 2

2,5-bis(methylthio)pyridine

To 75 ml of decahydronaphthalene was added portionwise while heating 59.5 g of 3,6-bis(methylthio)-2-pyridinecarboxylic acid. When the mixture reached 155° C., gas bubbles began to appear. The reaction was heated at 175° C. until no more bubbles appeared. Upon cooling the decahydronaphthalene solution was treated with 40 ml of 6 normal (N) HCl in three portions resulting in the formation of a solid which was collected. The solid was covered with water. The aqueous layer and solid were then made basic with 50% NaOH and extracted with ether. The ether solution was treated with charcoal, dried and the ether removed, which gave 31 g (66% yield) of a yellow oil. A portion of this oil was placed on a Kügelrohr distillation apparatus and the product, 2,5-bis(methylthio)pyridine recovered, at 90° C. at a pressure of 0.1 mm Hg.

EXAMPLE 3

2,5-bis(methylsulfonyl)pyridine 2,5-bis(Methylthio)pyridine (26 g) was dissolved in 60 ml of acetic acid and 75 g of 30% hydrogen peroxide ($H_2O_2$) was added dropwise. After about $\frac{1}{4}$–$\frac{1}{3}$ of the oxidant had been added, the reaction exothermed to 95° C. Addition was stopped and the reaction was cooled to 75° C. with an ice bath. The addition was resumed and the temperature was kept at 75° C. for 4 hours. After cooling, the solid was recovered by filtration and then washed with water, ethanol and ether. A portion of the solid was recrystallized from acetonitrile which gave 2,5-bis(methylsulfonyl)pyridine as a white solid, m.p. 205°–207° C.

EXAMPLE 4

2,5-bis(ethylsulfonyl)pyridine

Sodium hydroxide (160 g) was weighed into a reaction flask, and covered with 1 liter of DMSO which was then cooled in an ice bath (~10° C.) and then 149 g of ethanethiol was added. The mixture was stirred at room temperature for 1 hour and then 3,6-dichloro-2-pyridinecarboxylic acid (192 g) was added and the resulting mixture was heated at 130° C. for 6 hrs. After cooling, the reaction mixture was poured into 5 kilograms (kg) of ice, and acidified with 140 ml of concentrated HCl. A solid formed which was collected by filtration. The aqueous filtrate was decanted into a separatory funnel and extracted with 2 liters of 1,1,1-trichloroethane. The solid was dissolved in 1 liter of $CH_2Cl_2$. The organic solutions were combined, washed with 1 liter of water, dried, and concentrated to give 273 g of crude 3,6-bis(ethylthio)-2-pyridinecarboxylic acid. The crude 3,6-bis(ethylthio)-2-pyridinecarboxylic acid was dissolved in 100 ml of 1,2-dichlorobenzene and added in small portions to 500 ml of 1,2-dichlorobenzene heated at 160° C. After the addition was complete, heated was continued for 2 hrs. The reaction mixture was chilled in ice and extracted three times with 200 ml of 6N HCl.

The acidic solution was put in a large container equipped with a mechanical stirrer. To this fast stirring solution was added 4 liters of 5.25% NaOCl solution. An off-white precipitate was formed which was collected by filtration, washed with water and dried to give 136.7 g of the product, 2,5-bis(ethylsulfonyl)pyridine, m.p. 148°–150° C.

EXAMPLE 5

2,5-bis((1-methylethyl)thio)pyridine

To 198 g of t-BuOK dissolved in 300 ml of DMF was added 2-propanethiol (163.47 ml) dropwise with an ice bath employed to keep the temperature below 50° C. As salt began to precipitate out an additional 50 ml of DMF was added. After addition was complete, the ice bath was removed and the mixture heated to 50° C. A solution of 100 g of methyl 3,6-dichloro-2-pyridinecarboxylate dissolved in DMF was added and the temperature during addition rose to 115° C. The temperature was then maintained at approximately 105°–110° C. until addition was completed and then the resulting mixture was heated at 100°–110° C. for 1½ hrs. The reaction mixture was allowed to cool and the solvent removed in a rotary evaporator. The brown residue which remained was washed with ether and then dissolved in water. The solution was acidified with HCl, and the product, which oiled out, extracted with $CH_2Cl_2$. The $CH_2Cl_2$ was then removed using a rotary evaporator. Infrared spectroscopy (IR) and nuclear magnetic resonance spectroscopy (NMR) indicated that 3,6-bis((1-methylethyl)thio)-2-pyridinecarboxylic acid had formed. The 3,6-bis((1-methylethyl)thio)-2-pyridinecarboxylic acid was decarboxylated employing a Kügelrohr distillation apparatus, and 2,5-bis((1-methylethyl)thio)pyridine obtained, b.p. 310° C. (760 mm Hg).

EXAMPLE 6

3,6-bis(n-hexylthio)-2-pyridinecarboxylic acid

To 300 ml of DMSO was added 84.5 g of powdered NaOH with vigorous stirring followed by the addition of 150 g of n-hexyl mercaptan. The anion of the mercaptan was allowed to form and then 111 g of 3,6-dichloro-2-pyridinecarboxylic acid in 110 ml of DMSO was added through a dropping funnel. The temperature was increased during addition to 135° C. and maintained at that temperature for 2½ hours. Upon cooling the brown solution was poured into three volumes of water. The resulting solution was acidified with HCl and extracted with 1,1,1-trichloroethane. The organic layer was dried over $MgSO_4$ and the solvent removed on a rotary evaporator. The reaction yielded 155 g (68% yield) of 3,6-bis(n-hexylthio)-2-pyridinecarboxylic acid as a dark oil which solidified on standing; m.p. 40°–42° C.

EXAMPLE 7

2,5-bis(n-hexylthio)pyridine

Crude 3,6-bis(n-hexylthio)-2-pyridinecarboxylic acid (140 g) was placed on a Kügelrohr distillation apparatus and heated to 135°–145° C. which resulted in the material spontaneously losing $CO_2$. When gas evolution had ceased, the temperature was raised. The product distilled over at 185°–195° C. (0.2 mm Hg) and 98 g (82% yield) of the product 2,5-bis(n-hexylthio)pyridine recovered as an oil.

EXAMPLE 8

2,5-bis(n-hexylsulfonyl)pyridine

In 400 ml of trifluoroacetic acid was dissolved 92.98 g of 2,5-bis(n-hexylthio)pyridine which was then heated to 50° C. The dropwise addition of 148.9 g of 30% aqueous $H_2O_2$ resulted in an exotherm which was controlled with a water bath, the temperature being kept below about 70°–75° C. After all of the 30% aqueous $H_2O_2$ was added, the reaction mixture was heated at 50°–55° C. for 1 hour. The reaction mixture was cooled to room temperature and then poured into 2 liters of cold water. The solid which formed was recovered by filtration and dried giving the crude product. A portion of the crude product was recrystallized from $CH_2Cl_2$/isopropanol and the resulting purified 2,5-bis(n-hexylsulfonyl)pyridine found to have a melting point of 135°–136° C.

EXAMPLE 9

3,6-bis(cyclohexylthio)-2-pyridinecarboxylic acid

The compound 3,6-bis(cyclohexylthio)-2-pyridinecarboxylic acid, m.p. 100°–101° C. was prepared by reacting 3,6-dichloro-2-pyridinecarboxylic acid and cyclohexyl mercaptan utilizing procedures substantially as described herein.

EXAMPLE 10

3,6-bis(phenylthio)-2-pyridinecarboxylic acid

In a reaction flask 50 g of methyl 3,6-dichloro-2-pyridinecarboxylate and 100 ml of DMF were placed. In a beaker were placed 90 g of t-BuOK and 200 ml of DMF, followed by 88.3 g of thiophenol. The slurry which formed was added portionwise to the reaction flask resulting in a temperature rise. The resulting reaction mixture was heated at 110° C. for 3 hrs. The solvent was removed from the reaction mixture under reduced pressure and the residual solid was dissolved in water and washed with diethyl ether. The aqueous layer was acidified and 58 g of crude product obtained. A portion of the crude product was recrystallized from methanol and the recrystallized 3,6-bis(phenylthio)-2-pyridinecarboxylic acid found to have a melting point of 131°–132° C.

EXAMPLE 11

3,6-bis((phenylmethyl)thio)-2-pyridinecarboxylic acid

In 400 ml of DMF was dissolved 198 g of t-BuOK. While the temperature was kept at 70°–90° C. with cooling, 218.6 g of benzylmercaptan was added. To this mixture was added 100 g of methyl 3,6-dichloro-2-pyridinecarboxylate in 100 ml of DMF without cooling. The temperature rose to 105° C. and the temperature was maintained at 105° C. for 1 hr. The solvent was removed under reduced pressure and the residual solid obtained washed with diethyl ether. The solid was dissolved in water and allowed to stand overnight. Two layers were observed. The upper layer was acidified with concentrated HCl to a pH of about 1–2 resulting in the formation of a solid which was collected by filtration. NMR spectroscopy indicated a mono-substituted compound. The lower layer was acidified, which gave 86 g (48% yield) of a solid. The solid obtained from the lower layer was recrystallized from 2-propanol to give the product, 3,6-bis((phenylmethyl)thio)-2-pyridinecarboxylic acid, m.p. 129° C.

EXAMPLE 12

2,3-bis(methylthio)pyridine

In a 4-necked flask equipped with a Dry Ice condenser, mechanical stirrer, thermometer and dropping funnel, 172.2 g of t-BuOK was dissolved in 200 ml of DMSO at room temperature with stirring under $N_2$. The solution was cooled with an ice bath while 50.0 g of methanethiol was added. The mixture was stirred for 30 minutes, then the ice bath was removed. A solution of 5,6-dichloro-2-pyridinecarboxylic acid (90.6 g) in 250 ml of DMSO was added at a rate such that the exotherm did not cause the temperature of the mixture to exceed 75° C. A dense slurry formed. An additional 500 ml of DMSO was added, and the slurry was stirred for 42 hours at 60° C. After cooling to room temperature, 500 ml of water was added to the reaction mixture, which was then added to 3.5 liters of ice water, and acidified to pH 1 with concentrated HCl. The yellow precipitate which formed was collected and dried which gave 87.33 g of a mixture of 5-chloro-6-(methylthio)-2-pyridinecarboxylic acid (~3.36 g) and 5,6-bis(methylthio)-2-pyridinecarboxylic acid (~83.97 g). The relative amounts of the 5-chloro-6-(methylthio)-2-pyridinecarboxylic acid and 5,6-bis(methylthio)-2-pyridinecarboxylic acid were estimated based on the amounts of the mono and bis-adducts isolated after decarboxylation.

A stirred solution of 250 ml of diphenyl oxide was heated to 200° C. A 54 g quantity of the 5-chloro-6-(methylthio)-2-pyridinecarboxylic acid/5,6-bis(methylthio)-2-pyridinecarboxylic acid mixture described above was added portionwise as a solid. The mixture was stirred for 1 hour with the temperature being maintained below 235° C. The mixture was cooled to 100° C., diluted with xylene and cooled to room temperature, then extracted three times with 75 ml of 6N HCl. The combined aqueous fractions were back-washed with diethyl ether, then stirred with $CH_2Cl_2$ and made strongly basic with 25% NaOH. The organic layer was separated, washed with water, then brine, and dried ($Na_2SO_4$). The solids were removed from the organic layer by filtration, then the filtrate was evaporated leaving a brown oil which was purified on a Kügelrohr distillation apparatus and 23.6 g of an oil obtained. The components of the oil were separated employing high pressure liquid chromatography (Porasil, 3% diethyl ether/hexane) and 19.42 g of 2,3-bis(methylthio)pyridine (b.p. 85° C. at 0.3 mm Hg) and 0.77 g of 3-chloro-2-(methylthio)pyridine (b.p. 80° C. at 0.3 mm Hg) obtained, both as colorless oils.

EXAMPLE 13

2,3-bis(methylsulfonyl)pyridine 2,3-bis(Methylthio)pyridine, (16 g) was dissolved in 40 ml of trifluoroacetic acid and stirred at room temperature, then 70 ml of 30% aqueous $H_2O_2$ was added dropwise. The mixture was heated at 50° C. for one hour, then cooled and poured onto ice. The resulting white solid was collected and dried to give 14.2 g of the crude product. A portion of the crude product was recrystallized from $CH_2Cl_2$/hexane which gave purified 2,3-bis(methylsulfonyl)pyridine, m.p. 175°–176.5° C.

EXAMPLE 14

5,6-bis(ethylthio)-2-pyridinecarboxylic acid

Potassium t-butoxide (111 g) was stirred in 200 ml of DMSO under $N_2$. The reaction vessel was cooled with an ice bath while ethanethiol (43 g) was added, and the mixture was stirred for 30 minutes. The cold bath was removed, and 5,6-dichloro-2-pyridinecarboxylic acid (55 g) in 300 ml of DMSO was added. The mixture was stirred at 75° C. for 20 hours. After cooling, the mixture was added to 2 liters of ice water, then acidified with concentrated HCl. The white solid which formed was collected and dried to give 66.15 g of the crude product. A portion of the crude product was recrystallized from isopropanol which gave purified 5,6-bis(ethylthio)-2-pyridinecarboxylic acid, m.p. 112°–113° C.

Other bis(R-thio)pyridines were prepared by the decarboxylation of the appropriate bis(R-thio)-2-pyridinecarboxylic acid using the procedures described herein. These compounds are:

EXAMPLE 15
2,5-bis(cyclohexylthio)pyridine

EXAMPLE 16
2,5-bis(phenylthio)pyridine

EXAMPLE 17
2,5-bis((phenylmethyl)thio)pyridine

EXAMPLE 18
2,3-bis(ethylthio)pyridine

Additional bis(R-sulfonyl)pyridines were prepared by oxidizing the appropriate bis(R-thio)pyridine using procedures described herein. These compounds are:

EXAMPLE 19
2,5-bis((1-methylethyl)sulfonyl)pyridine

EXAMPLE 20
2,5-bis(cyclohexylsulfonyl)pyridine

EXAMPLE 21
2,5-bis(phenylsulfonyl)pyridine

EXAMPLE 22
2,5-bis((phenylmethyl)sulfonyl)pyridine

EXAMPLE 23
2,5-bis(ethylsulfonyl)pyridine

The physical properties of the above examples are summarized in Table 1.

TABLE 1

| Compound Example Number | M.p. °C.* B.p. (mm Hg) | Calculated % C | % H | % N | Found % C | % H | % N |
| --- | --- | --- | --- | --- | --- | --- | --- |
| 1 | 142–144 | 44.63 | 4.21 | 6.51 | 44.58 | 4.22 | 6.42 |
| 2 | 90 (0.1) | 49.08 | 5.30 | 8.18 | 49.78 | 5.35 | 8.04 |
| 3 | 205–207 | 35.73 | 3.86 | 5.95 | 35.91 | 3.97 | 5.98 |
| 4 | 148–150 | 41.05 | 4.97 | 5.32 | 40.63 | 5.02 | 5.33 |
| 5 | 310 (760) | 58.10 | 7.54 | 6.16 | 57.10 | 7.01 | 6.18 |
| 6 | 40–42 | 60.80 | 8.22 | 3.94 | 58.62 | 7.96 | 3.60 |
| 7 | 185–195 (0.2) | 65.54 | 9.38 | 4.50 | 64.22 | 9.03 | 4.31 |
| 8 | 135–136 | 54.37 | 7.78 | 3.73 | 54.13 | 7.77 | 3.70 |
| 9 | 100–101 | 61.50 | 7.17 | 3.99 | 61.09 | 7.26 | 4.29 |
| 10 | 131–132 | 63.69 | 3.86 | 4.13 | 63.32 | 3.96 | 4.05 |
| 11 | 129 | 65.37 | 4.66 | 3.81 | 64.99 | 4.85 | 3.65 |
| 12 | 85 (0.3) | 49.08 | 5.30 | 8.18 | 49.05 | 5.12 | 8.09 |
| 13 | 175–176.5 | 35.73 | 3.86 | 5.95 | 35.35 | 3.80 | 5.68 |
| 14 | 112–113 | 49.35 | 5.38 | 5.76 | 49.24 | 5.53 | 5.66 |
| 15 | 177–190 (0.5) | 66.39 | 8.19 | 4.56 | 65.49 | 7.97 | 4.13 |
| 16 | 190 (0.05) | 69.12 | 4.43 | 4.74 | 68.64 | 4.51 | 4.82 |
| 17 | 77 | 70.55 | 5.30 | 4.33 | 70.49 | 5.32 | 4.33 |
| 18 | 95 (0.3) | 54.23 | 6.57 | 7.03 | 54.11 | 6.48 | 7.00 |
| 19 | 181 | 45.34 | 5.88 | 4.81 | 45.47 | 5.88 | 4.73 |
| 20 | 213 | 54.96 | 6.78 | 3.77 | 54.80 | 6.93 | 3.91 |
| 21 | 202–205 | 56.81 | 3.64 | 3.90 | 56.88 | 3.75 | 3.99 |
| 22 | 265 (d)** | 58.89 | 4.42 | 3.62 | 58.29 | 4.52 | 3.57 |
| 23 | 132 | 41.05 | 4.97 | 5.32 | 41.08 | 5.06 | 5.29 |

*The values presented refer to either the melting point in degrees Centigrade or the boiling point in degrees Centigrade at a particular pressure indicated in millimeters of mercury.
**The symbol "(d)" means that the compound decomposed at the indicated temperature.

EXAMPLE 24

5-(methylsulfonyl)-2-(4-((trifluoromethyl)thio)phenoxy)pyridine

To 4.95 g of 4-(trifluoromethylthio)phenol dissolved in a 20 ml THF/20 ml DMSO mixture was added 2.9 g of t-BuOK and then 6.0 g of 2,5-bis(methylsulfonyl)pyridine, and the resulting mixture heated at 58° C. for 1½ hrs. The reaction mixture was cooled to room temperature and added to approximately 3 to 4 volumes of water. The yellow-brown precipitate that formed was removed by filtration and then recrystallized from $CH_2Cl_2$/ethanol. The purified product, 5-(methylsulfonyl)-2-(4-((trifluoromethyl)thio)phenoxy)pyridine, (60% yield), was recovered as tiny cream-white plates, m.p. 134°–135° C.

Elemental Analysis: Theoretical: Carbon-44.69%; Hydrogen-2.89%; Nitrogen-4.01%; Found: Carbon-44.98%; Hydrogen-3.03%; Nitrogen-4.03%

EXAMPLE 25

5-(ethylsulfonyl)-2-(3,4-methylenedioxyphenoxy)pyridine

Into a reaction flask was weighed 5.6 g of t-BuOK and then 50 ml of THF was added. In 50 ml of DMSO was dissolved 6.2 g of 3,4-methylenedioxyphenol which was then slowly added to the t-BuOK solution with stirring. To the resulting potassium phenate solution was added 10.5 g of 2,5-bis(ethylsulfonyl)pyridine and this mixture heated at 50°–55° C. for 3 hrs. After cooling, the reaction mixture was poured into 400 g of ice, stirred and then filtered. The solid which was recovered was dissolved in $CH_2Cl_2$, treated with charcoal, dried over $MgSO_4$ and then filtered. The $CH_2Cl_2$ solution was concentrated to 50 ml, diluted with an equal volume of hexane and then chilled and a crystalline material recovered, which provided 9.9 g, (80% yield), of 5-(ethylsulfonyl)-2-(3,4-methylenedioxyphenoxy)pyridine, m.p. 97°–99° C.

Elemental Analysis: Theoretical: Carbon-54.71%; Hydrogen-4.26%; Nitrogen-4.56%; Found: Carbon-54.67%; Hydrogen-4.31%; Nitrogen-4.65%

EXAMPLE 26

2-(3,4-dichlorophenoxy)-5-((1-methylethyl)sulfonyl)pyridine

To 4.89 g of 3,4-dichlorophenol dissolved in a 25 ml THF/25 ml DMSO mixture was added 3.2 g of t-BuOK and then 8.74 g of 2,5-bis((1-methylethyl)sulfonyl)pyridine, and the resulting mixture was heated at 58° C. for 1½ hrs. The reaction mixture was allowed to cool overnight and then poured in approximately 3 to 4 volumes of water and stirred. The yellow-white precipitate which formed was removed by filtration. Recrystallization from $CH_2Cl_2$/ethanol gave the product, 2-(3,4-dichlorophenoxy)-5-((1-methylethyl)sulfonyl)pyridine, (42% yield), as tiny white needles, m.p. 91°–92° C.

Elemental Analysis: Theoretical: Carbon-48.56%; Hydrogen-3.78%; Nitrogen-4.05%; Found: Carbon-48.92%; Hydrogen-3.82%; Nitrogen-3.95%

EXAMPLE 27

2-(4-bromophenoxy)-5-(n-hexylsulfonyl)pyridine

To 4.33 g of 4-bromophenol dissolved in a 22 ml THF/22 ml DMSO mixture was added 3.1 g of t-BuOK and then 9.39 g of 2,5-bis(n-hexylsulfonyl)pyridine, and the resulting mixture heated at 59° C. for 1 hr. The reaction mixture was cooled to room temperature and then added to approximately 4 to 5 volumes of water. The yellow precipitate which formed was removed by filtration. Recrystallization from $CH_2Cl_2$/ethanol gave the product, 2-(4-bromophenoxy)-5-(n-hexylsulfonyl)pyridine, (52% yield), as white shiny prisms, m.p. 94° C.

Elemental Analysis: Theoretical: Carbon-51.26%; Hydrogen-5.06%; Nitrogen-3.52%; Found: Carbon-50.92%; Hydrogen-5.13%; Nitrogen-3.62%

EXAMPLE 28

1-(4-((5-(cyclohexylsulfonyl)-2-pyridinyl)oxy)phenyl)ethanone

To 3.68 g of p-hydroxyacetophenone in a 25 ml THF/25 ml DMSO mixture was added 3.2 g of t-BuOK and then 10.03 g of 2,5-bis(cyclohexylsulfonyl)pyridine, and the resulting mixture was heated at 62° C. for 1½ hrs. The reaction mixture was cooled overnight, then added to 4 volumes of water and the crude product which formed recovered by filtration. Recrystallization of the crude product from $CH_2Cl_2$/ethanol gave the product, 1-(4-((5-(cyclohexylsulfonyl)-2-pyridinyl)oxy)phenyl)ethanone, (31% yield), as light yellow prisms, m.p. 116°–118° C.

Elemental Analysis: Theoretical: Carbon-63.48%; Hydrogen-5.89%; Nitrogen-3.90%; Found: Carbon-62.72%; Hydrogen-6.10%; Nitrogen-3.99%

EXAMPLE 29

2-(3,4-dichlorophenoxy)-5-(phenylsulfonyl)pyridine

To 4.08 g of 3,4-dichlorophenol dissolved in a 25 ml THF/25 DMSO mixture was added 2.9 g of t-BuOK and then 8.99 g of 2.5-bis(phenylsulfonyl)pyridine, and the resulting mixture heated at 58° C. for 1½ hrs. The reaction mixture was cooled to room temperature, then added to 3 to 4 volumes of water and stirred. The brown precipitate which formed was removed by filtration. Recrystallization from $CH_2Cl_2$/ethanol gave the purified product, 2-(3,4-dichlorophenoxy)-5-(phenylsulfonyl)pyridine (68% yield), as white shiny needles, m.p. 113°–114° C.

Elemental Analysis: Theoretical: Carbon-53.69%; Hydrogen-2.92%; Nitrogen-3.68%; Found: Carbon-53.47%; Hydrogen-3.09%; Nitrogen-3.57%

EXAMPLE 30

Phenyl(4-((5-((phenylmethyl)sulfonyl)-2-pyridinyl)oxy)phenyl)methanone

To 4.96 g of p-hydroxybenzophenone in a 25 ml THF/25 ml DMSO mixture was added 3.1 g of t-BuOK and then 9.69 g of 2,5bis((phenylmethyl)sulfonyl)pyridine and the resulting mixture heated at 60° C. for 1½ hrs. The reaction mixture was allowed to cool overnight, diluted with 4 volumes of water, and the golden-brown precipitate which formed removed by filtration. Recrystallization from $CH_2Cl_2$/ethanol and then from toluene gave the product, phenyl(4-((5-((phenylmethyl)sulfonyl)-2-pyridinyl)oxy)phenyl)methanone, (44% yield), as tan prisms, m.p. 146°–147° C.

Elemental Analysis: Theoretical: Carbon-69.91%; Hydrogen-4.46%; Nitrogen-3.26%; Found: Carbon-69.61%; Hydrogen-4.66%; Nitrogen-3.12%

EXAMPLE 31

2-(3,4-dichlorophenoxy)-3-(methylsulfonyl)pyridine

Potassium t-butoxide (2.47 g) was dissolved in 30 ml of THF and then 3.46 g of 3,4-dichlorophenol dissolved in THF was added. A solution of 5.00 g of 2,3-bis(methylsulfonyl)pyridine in 20 ml THF/20 ml DMSO was added dropwise. The resulting mixture was stirred at room temperature for 3 hours. The reaction mixture was poured onto ice-water which resulted in the formation of an oil which solidified on standing. The product was collected by filtration and dried in a vacuum oven and 5.33 g of material obtained. Recrystallization from $CH_2Cl_2$/hexane gave purified 2-(3,4-dichlorophenoxy)-3-(methylsulfonyl)pyridine, m.p. 95°–96° C.

Elemental Analysis: Theoretical: Carbon-45.29%; Hydrogen-2.85%; Nitrogen-4.40%; Found: Carbon-45.16%; Hydrogen-2.80%; Nitrogen-4.22%

EXAMPLE 32

(4-((3-(ethylsulfonyl)-2-pyridinyl)oxy)phenyl)phenylmethanone

Potassium t-butoxide (4.78 g) was stirred in 30 ml of DMSO at room temperature. p-Hydroxybenzophenone (7.82 g) in 30 ml of THF was added and stirred for 15 minutes. A solution of 2,3-bis(ethylsulfonyl)pyridine (7.8 g) in 30 ml of DMSO was added. The mixture was stirred for 2 hours, then poured onto ice. The tan solid which formed was collected and dried and 8.31 g of solid obtained. The solid was dissolved in $CH_2Cl_2$ and filtered through a short $SiO_2$ plug with ethyl acetate/hexane (1:1). The solvents were concentrated to cause crystallization. The white crystals were collected and dried to give 5.21 g of the product, (4-((3-(ethylsulfonyl)-2-pyridinyl)oxy)phenyl)phenylmethanone, m.p. 149° C.

Elemental Analysis: Theoretical: Carbon-65.37%; Hydrogen-4.66%; Nitrogen-3.81%; Found: Carbon-65.35%; Hydrogen-4.70%; Nitrogen-3.76%

Antiviral activity was demonstrated for the compounds of Examples 24–32 using the following Tissue Culture testing procedure:

Monolayered HeLa cells in 16 millimeter (mm) tissue culture dishes were treated with 1 ml of culture medium (Eagles medium supplemented with fetal calf serum) containing subject compound at an appropriate concentration or containing no compound at all. Culture media such as those described herein are more fully described in standard texts, as for example, Kuchler's Biochemical Methods in Cell Culture and Virology, Dowden, Hutchinson and Ross, Inc., Stroudsberg, PA (1977). Following treatment, cells were challenged with 0.05 ml of rhinovirus type 1A (RV-1A), rhinovirus type 2 (RV-2) or Coxsackie $A_{21}$ virus (Cox $A_{21}$) in culture medium. Some of the compounds were also tested against rhinovirus type 5 (RV-5), rhinovirus type 8 (RV-8) or rhinovirus type 64 (RV-64). Cell controls received no viruses. Cultures were observed for compound cytotoxicity and viral cytopathic effect (CPE) at 48 and 72 hours post-treatment.

The results obtained from the Tissue Culture testing of the compounds of Examples 24–32 are summarized in Table 2.

TABLE 2

| Example Number | Cytotoxicity[1] (μg/ml) | Tissue Culture Testing[2] (μg/ml) | | | | | |
|---|---|---|---|---|---|---|---|
| | | RV-1A | RV-2 | Cox $A_{21}$ | RV-5 | RV-8 | RV-64 |
| 24 | ≧100 | 12.5 | <6.25 | <6.25 | NA | NA | <6.25 |
| 25 | ≧50 | NA | 25 | NA | | | NA |
| 26 | 12.5 | <0.3125 | 0.625 | 0.625 | NA | NA | 0.625 |
| 27 | >50 | 25 | 25 | 12.5 | | | |
| 28 | 12.5 | ±12.5 | ±12.5 | 3.125 | | | |
| 29 | ≧100 | 5 | 10 | 10 | | | |
| 30 | 50 (GI) | 25 | NA | <3.125 | | | |
| 31 | 50 | 25 | 50 | 50 | | | |
| 32 | 50 | 50 | ±50 | NA | | | |

[1]Cytotoxicity figures represent the concentration of the compound, micrograms/milliliter (μg/ml), found to be toxic to the cell.
[2]Lowest concentration of the compound (μg/ml) necessary to cause a 50 percent reduction in cytopathic effect.
The symbol "NA" indicates that the compound was not active against that particular virus at the standard test conditions; "<" means "less than"; ">" means "greater than"; "≦" means "greater than or equal to"; "±" means "approximately"; "GI" means "growth inhibition" and indicates that at the concentration shown the compound inhibited the growth of the tissue culture.

Other compounds exhibiting antiviral activity in the Tissue Culture testing were prepared according to the procedures described herein. These compounds are:

5-(methylsulfonyl)-2-(4-phenoxyphenoxy)pyridine, m.p. 136.5°–138° C.

2-(4-bromophenoxy)-5-(methylsulfonyl)pyridine, m.p. 125°–126° C.

4-((5-(methylsulfonyl)-2-pyridinyl)oxy)benzonitrile, m.p. 195°–196° C.

(4-((5-(methylsulfonyl)-2-pyridinyl)oxy)phenyl)phenylmethanone, m.p. 130°–131.5° C.

2-(4-chlorophenoxy)-5-(methylsulfonyl)pyridine, m.p. 117°–118° C.

2-(4-(1,1-dimethylethyl)phenoxy)-5-(methylsulfonyl)pyridine, m.p. 142° C.

1-(4-((5-(methylsulfonyl)-2-pyridinyl)oxy)phenyl)ethanone, m.p. 143°–144° C.

2-(3-bromophenoxy)-5-(methylsulfonyl)pyridine, m.p. 134.5° C.

3-((5-(methylsulfonyl)-2-pyridinyl)oxy)benzonitrile, m.p. 139° C.

2-(4-(methylthio)phenoxy)-5-(methylsulfonyl)pyridine, m.p. 128°–130° C.

2-(3,4-dichlorophenoxy)-5-(methylsulfonyl)pyridine, m.p. 120°–121° C.

2-(4-chlorophenoxy)-5-(ethylsulfonyl)pyridine, m.p. 128°–130° C.

(4-((5-(ethylsulfonyl)-2-pyidinyl)oxy)phenyl)phenylmethanone, m.p. 131°–132° C.

5-(ethylsulfonyl)-2-(4-phenoxyphenoxy)pyridine, m.p. 38°–41° C.

2-(3,4-dichlorophenoxy)-5-(ethylsulfonyl)pyridine, m.p. 117°–118° C.

5-(ethylsulfonyl)-2-(2,4,5-trichlorophenoxy)pyridine, m.p. 120°–122° C.

2-(4-bromophenoxy)-5-((1-methylethyl)sulfonyl)pyridine, m.p. 93°–94° C.

(4-((5-((1-methylethyl)sulfonyl)-2-pyridinyl)oxy)phenyl)phenylmethanone, m.p. 113°–114° C.

1-(4-((5-((1-methylethyl)sulfonyl)-2-pyridinyl)oxy)phenyl)ethanone, m.p. 114°–115° C.

2-(3,4-dichlorophenoxy)-5-(n-hexylsulfonyl)pyridine, m.p. 75.5° C.

(4-((5-(n-hexylsulfonyl)-2-pyridinyl)oxy)phenyl)phenylmethanone, m.p. 72°–74° C.

2-(4-bromophenoxy)-5-(cyclohexylsulfonyl)pyridine, m.p. 146.5°–147° C.

2-(3,4-dichlorophenoxy)-5-(cyclohexylsulfonyl)pyridine, m.p. 114° C.

(4-((5-(cyclohexylsulfonyl)-2-pyridinyl)oxy)phenyl)phenylmethanone, m.p. 138°–139° C.

2-(4-bromophenoxy)-5-(phenylsulfonyl)pyridine, m.p. 120°–121° C.

2-(3,4-dichlorophenoxy)-5-((phenylmethyl)sulfonyl)pyridine, m.p. 112°–113° C.

2-(4-bromophenoxy)-5-((phenylmethyl)sulfonyl)pyridine, m.p. 130° C.

(4-((3-(methylsulfonyl)-2-pyridinyl)oxy)phenyl)phenylmethanone, m.p. 119°–120° C.

2-(3,4-dichlorophenoxy)-3-(ethylsulfonyl)pyridine, m.p. 82° C.

Some of the above-noted compounds demonstrated antiviral activity in animals utilizing "Single Oral Dose" and "Continuous Oral Feeding" test procedures; the test procedures employed were substantially the same as those described in U.S. Pat. No. 4,254,144.

What is claimed is:

1. A compound of the formula:

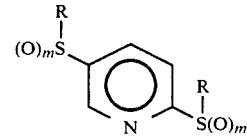

wherein m represents the integer 0 or 2; and R represents an alkyl group of from 1 to 7 carbon atoms, inclusive, cyclopentyl, cyclohexyl, or a Ar—$(CH_2)_q$— group wherein q represents the integer 0, 1, 2 or 3 and Ar represents a phenyl or naphthyl group, which phenyl or naphthyl group is optionally substituted with 1 to 3 substituents each independently selected from bromo, chloro, fluoro, methyl or methoxy.

2. The compound of claim 1 wherein m is 0.

3. The compound of claim 1 wherein m is 2.

4. The compound of claim 1 wherein R is an alkyl group.

5. The compound of claim 4 wherein R is methyl or ethyl.

6. The compound of claim 1 wherein R is cyclohexyl.

7. The compound of claim 1 wherein R is phenyl or benzyl.

8. The compound of claim 1 which is 2,5-bis(methylthio)pyridine.

9. The compound of claim 1 which is 2,5-bis(methylsulfonyl)pyridine.

10. The compound of claim 1 which is 2,5-bis(ethylsulfonyl)pyridine.

11. The compound of claim 1 which is 2,5-bis((1-methylethyl)thio)pyridine.

12. The compound of claim 1 which is 2,5-bis(n-hexylthio)pyridine.

13. The compound of claim 1 which is 2,5-bis(n-hexylsulfonyl)pyridine.

14. The compound of claim 1 which is 2,5-bis(cyclohexylthio)pyridine.

15. The compound of claim 1 which is 2,5-bis(phenylthio)pyridine.

16. The compound of claim 1 which is 2,5-bis((phenylmethyl)thio)pyridine.

17. The compound of claim 1 which is 2,5-bis((1-methylethyl)sulfonyl)pyridine.

18. The compound of claim 1 which is 2,5-bis(cyclohexylsulfonyl)pyridine.

19. The compound of claim 1 which is 2,5-bis(phenylsulfonyl)pyridine.

20. The compound of claim 1 which is 2,5-bis((phenylmethyl)sulfonyl)pyridine.

* * * * *

UNITED STATES PATENT AND TRADEMARK OFFICE
CERTIFICATE OF CORRECTION

PATENT NO. : 4,616,087

DATED : Oct. 7, 1986

INVENTOR(S) : Steven G. Wood

It is certified that error appears in the above-identified patent and that said Letters Patent is hereby corrected as shown below:

Cover sheet, Abstract, line 2 "substituted" should read "substituent".

Column 1, line 21 "R-R-" should read "R-S-".

Column 2, line 54 "(DME)" should read "(DMF)".

Column 5, line 68 "heated" should read "heating".

Column 9, line 49 "2,5-bis(" should read "2,3-bis(".

Column 11, line 55 "/25 DMSO" should read "/25 ml DMSO".

Column 11, line 56 "2.5" should read "2,5".

Column 12, line 7, "2,5bis" should read "2,5-bis".

Column 13, line 63, "-2-pyidinyl)" should read "-2-pyridinyl)".

Signed and Sealed this

Twenty-eighth Day of April, 1987

*Attest:*

DONALD J. QUIGG

*Attesting Officer*     *Commissioner of Patents and Trademarks*